United States Patent
Paul

(10) Patent No.: US 7,429,317 B2
(45) Date of Patent: Sep. 30, 2008

(54) ELECTROKINETIC DEVICE EMPLOYING A NON-NEWTONIAN LIQUID

(75) Inventor: Phillip H. Paul, Livermore, CA (US)

(73) Assignee: Eksigent Technologies LLC, Dublin, CA (US)

( * ) Notice: Subject to any disclaimer, the term of this patent is extended or adjusted under 35 U.S.C. 154(b) by 51 days.

(21) Appl. No.: 11/019,917

(22) Filed: Dec. 20, 2004

(65) Prior Publication Data

US 2006/0131174 A1     Jun. 22, 2006

(51) Int. Cl.
*F16K 7/17* (2006.01)

(52) U.S. Cl. .................. 204/600; 204/450; 251/61.1; 251/129.06

(58) Field of Classification Search ........... 204/450, 204/600; 251/61.1, 129.06
See application file for complete search history.

(56) References Cited

U.S. PATENT DOCUMENTS

| | | | |
|---|---|---|---|
| 3,923,426 A | | 12/1975 | Theeuwes |
| 3,952,577 A | * | 4/1976 | Hayes et al. ............. 73/54.04 |
| 6,013,164 A | | 1/2000 | Paul et al. |
| 6,019,882 A | | 2/2000 | Paul et al. |
| 6,068,752 A | * | 5/2000 | Dubrow et al. ............ 204/604 |
| 6,090,251 A | * | 7/2000 | Sundberg et al. .......... 204/453 |
| 6,224,728 B1 | | 5/2001 | Oborny et al. |
| 6,719,535 B2 | | 4/2004 | Rakestraw et al. |
| 7,258,777 B2 | | 8/2007 | Paul et al. |
| 2001/0052460 A1 | * | 12/2001 | Chien et al. ............... 204/450 |
| 2002/0189947 A1 | | 12/2002 | Paul et al. |
| 2004/0074768 A1 | * | 4/2004 | Anex et al. ............... 204/294 |

OTHER PUBLICATIONS

Manz et al, J. Micromech. Microeng., 4, 1994, pp. 257-265.*
Bello et al, Electrophoresis, 1994, 15, pp. 623-626.*
Buchholz et al, Electrophoresis, 2002, 23, pp. 1398-1409.*
Boger, D.V., "Demonstration of Upper and Lower Newtonian Fluid Behavior in a Pseudoplastic Fluid," Nature, vol. 265, No. 5589, Jan. 6, 1977, pp. 126-128.
Hunter, R.J., "Foundations of Colloid Science, vol. II," Oxford University Press, Oxford, 1989, pp. 994-1002.
Johnson, D.L. et al, "Theory Of Dynamic Permeability And Tortuosity In Fluid-Saturated Porous Media," Journal of Fluid Mechanics, vol. 176, Mar. 1987, pp. 379-402.
International Search Report for International Application No. PCT/US05/45674, dated Jan. 11, 2007, 3 pages.
Notification Concerning Transmittal and International Preliminary Report on Patentability and Written Opinion for International Application No. PCT/US05/45674, dated Jun. 26, 2007, 8 pages.

* cited by examiner

*Primary Examiner*—Kaj K Olsen
(74) *Attorney, Agent, or Firm*—Sheldon Mak Rose & Anderson PC

(57) ABSTRACT

A non-Newtonian fluid is used in an electrokinetic device to produce electroosmotic flow therethrough. The nonlinear viscosity of the non-Newtonian fluid allows the electrokinetic device to behave differently under different operating conditions, such as externally applied pressures and electric potentials. Electrokinetic devices can be used with a non-Newtonian fluid in a number of applications, including but not limited to electrokinetic pumps, flow controllers, diaphragm valves, and displacement systems.

15 Claims, 2 Drawing Sheets

ELECTROKINETIC DEVICE EMPLOYING A NON-NEWTONIAN LIQUID

BACKGROUND

1. Field of the Invention

This invention relates generally to electrokinetic fluidic devices, and in particular to the use of non-Newtonian liquids in electrokinetic fluidic devices.

2. Background of the Invention

Electrokinetic, or electroosmotic, flow is a well-known phenomenon. An electrokinetic fluidic (EOF) device typically includes a liquid-filled conduit that has an inlet and an outlet and may also contain porous material. The interior wetted surfaces of the conduit and any material disposed within the conduit display a zeta potential, which describes an electrical potential that exists across the interface between the conduit and the wetting fluid. In use, an electrical potential difference and/or a fluidic pressure-difference are applied between the inlet and the outlet.

A key parameter used to characterize an electrokinetic device is the electroosmotic mobility, which is given according to the classical Helmholtz-Smoluchowski formula as the product of the zeta potential and the liquid dielectric permittivity divided by the liquid dynamic viscosity.

Another key parameter is the Debye length in the liquid. The liquid in an electrokinetic device is ironically conducting due to the presence of some concentration of ionic particles in the liquid. The ionic particles can be any combination of salts or buffers that are fully dissolved or partially dissolved in the liquid. The combination of ionic particles is characterized by an ionic strength. The Debye length is inversely proportional to the square root of this ionic strength. In water at ambient temperature, for example, the Debye length is about 13.6 nanometers divided by the square root of the ionic strength, with ionic strength taken in units of millimoles per liter.

A third key parameter is the effective inside diameter of the conduit, called the pore scale. For a conduit of irregular cross-sectional shape, a conduit that contains sections that are subdivided (e.g., a bundle of capillaries), or a conduit that contains sections of porous material, a method for determining the pore scale is described in Johnson et al. [D. L. Johnson, J. Koplik and R. Dashen, "Theory of dynamic permeability and tortuosity in fluid-saturated porous media," F. Fluid Mech. vol. 176 pp. 379-402 (1987).].

For conditions where the pore scale is substantially greater than the Debye length (e.g., the pore scale is more than 100 times larger than the Debye length), the electroosmotic flow can be treated as ideal. For ideal electroosmotic flow, the electroosmotic mobility may be given by the classical Helmholtz-Smoluchowski formula. But where the pore scale is less than about 100 times the Debye length, several non-ideal processes become important: (1) The electroosmotic mobility is reduced; (2) The electrical conductivity of the liquid within the conduit is increased; and (3) Electrical conduction and electroosmosis pro flux through the conduit that causes a reduction of ionic concentration at the inlet of the conduit, which is inherently unstable. These non-ideal effects are amplified as the zeta potential is increased and/or the pore scale is decreased.

To maximize the classical electroosmotic mobility, the electrokinetic arts teach the use of a high zeta potential with liquids that have a high ratio dielectric permittivity per dynamic viscosity. Under ideal conditions, the volumetric flow rate produced by an electrokinetic device is equal to the electric current through the conduit times the electroosmotic mobility divided by the electrical conductivity of the liquid.

The maximum pressure (e.g., the stall pressure) produced by an electrokinetic device is then equal to 32 times the electroosmotic mobility times the liquid dynamic viscosity times the voltage applied across the device divided by the square of the pore scale of the device.

A liquid that displays a linear and proportional relationship between shear stress and shear rate is called a Newtonian liquid. For a Newtonian liquid, the shear stress is equal to the product of shear rate and liquid dynamic viscosity. Traditional electrokinetic devices use Newtonian liquids. Because Newtonian liquids have a constant ratio of shear stress to shear rate, the viscosity of the liquid under electroosmotically driven conditions is equal to that under pressure driven conditions. In classical electroosmotic devices, therefore, both the electroosmotic-and pressure-driven flow rates are inversely proportional to the same liquid viscosity.

In many practical applications, electrokinetic devices are designed to produce flow through some external flow resistance, which allows them to produce flow of a fluid against a backpressure. This has been accomplished by balancing the use of small pore size to provide a high stall pressure (hence the need to increase ionic strength to avoid non-ideal effects) against reducing ionic strength to minimize the current required to provide flow. High current is preferably avoided to avoid Joule-heating that can lead to thermal runaway and to reduce electrochemical evolution of the liquid at the electrodes that are positioned at the terminal ends of the electrokinetic device.

SUMMARY OF THE INVENTION

To overcome limitations inherent in traditional electrokinetic devices, various embodiments of the invention take advantage of the properties of non-Newtonian fluids. Non-Newtonian fluids exhibit a nonlinear relationship between shear rate and shear stress. This nonlinear relationship allows an electrokinetic device to behave in one way under one set of operating conditions and in another way under a different set of operating conditions. When used with non-Newtonian fluids, therefore, electrokinetic devices can be made to operate at performance levels impossible with traditional electrokinetic methods, which rely on Newtonian fluids. This enhanced performance ability enables operation of electrokinetic devices in flow-pressure regimes that would be impractical using traditional electrokinetic methods.

Different operating conditions for an electrokinetic device may arise, for example, under pressure driven flow versus those under electroosmotically driven flow. For electroosmotic flow, the high shear stress at the walls of the device makes the electroosmotic flow rate inversely proportional to the viscosity of the liquid for high stresses. For pressure driven flow, the relatively low maximum shear stress makes the pressure driven flow rate inversely proportional to values of viscosity approaching or equal to the viscosity at low stresses. With a non-Newtonian liquid having a low-stress viscosity of many times greater (e.g., 1000 or more times greater) than the high-stress viscosity, the pressure driven flow experiences substantially more viscous flow resistance than the electroosmotic flow. This has many applications as described below.

In one embodiment of the invention, an electrokinetic device comprises a conduit having an inlet, an outlet, and an interior surface. The interior surface of the conduit, including any internal subdivisions or any porous material within the conduit, displays a zeta potential when a non-Newtonian liquid is placed within the conduit in contact with its surface. The zeta potential characterizes some amount of net charge in the liquid that is located at the interface between the liquid and the bounding solid. The non-Newtonian liquid is preferably an ironically conducting liquid that exhibits a substantial nonlinear relationship between shear rate and shear stress. An electric potential is configured across the inlet and outlet of the conduit for applying an electric field along the axis of the conduit. This electric field imposes a body force on the net charge in the liquid, resulting in electroosmotic flow. In another embodiment, a kit for operating an electrokinetic device includes a conduit and a source of electric potential with instructions for using the device with a non-Newtonian liquid.

In another embodiment, an electrokinetic device is used as a pump to force the fluid to flow through the conduit and one or more flow resistive elements coupled to the outlet of the conduit. Another embodiment uses an electrokinetic device in a flow controller, where flow of liquid from a reservoir through a downstream flow resistive element is regulated by an electroosmotic flow through an electrokinetic conduit coupled between the reservoir and the flow resistive element. In another embodiment, a diaphragm valve includes a flexible member that is actuated between closed and open positions by an electroosmotic flow. It can thus be appreciated that a number of configurations, uses, and applications are possible for embodiments of the invention, using a non-Newtonian fluid with an electrokinetic device.

DETAILED DESCRIPTION OF THE PREFERRED EMBODIMENTS

Figure 1:
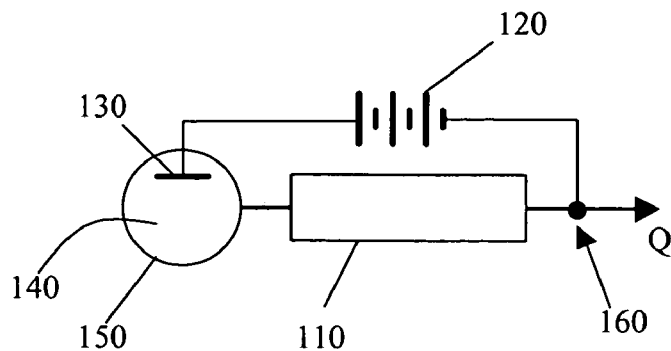
FIG. 1 is a schematic drawing of an electrokinetic device, in accordance with an embodiment of the invention.

Electrokinetic devices can be used in various configurations as elements within a fluid system to achieve a number of purposes. The basic theory and several applications of electrokinetic devices are described in co-owned U.S. Pat. No. 6,719,535, which is incorporated by reference in its entirety. FIG. 1 illustrates a basic system for producing electrokinetic fluid flow.

As shown, the electrokinetic device includes a conduit 110 that has an electrokinetically active interior. The conduit 110 is fluidically coupled to a reservoir 150 at one end of the conduit 110 (e.g., the inlet) and is free at an opposite end (e.g., the outlet). A liquid 140 fills the reservoir 150 and may be free to flow into the conduit 110 from its inlet and out of the conduit 110 through its outlet. Preferably, the liquid 140 also fills the conduit 110. The liquid 140 comprises a non-Newtonian liquid, which includes any liquid that exhibits a nonlinear relationship between shear stress and shear rate—i.e., a nonlinear viscosity.

Electrode 130 contacts the liquid 140 in the reservoir 150, and node 160 contacts the liquid at or near the outlet of the conduit 110. In other embodiments, the power supply 120 need not be in direct contact with the liquid 140, but instead is coupled to a source for generating an electric field within the conduit 110 (e.g., using capacitor plates). Node 160 may have a direct electrical connection to the liquid, or it may include a bridge connection. Suitable bridge connections for this purpose are described in co-owned U.S. patent application Ser. No. 10/896,102, filed Jul. 20, 2004, now U.S. Pat. No. 7,258,777 which is incorporated by reference in its entirety. Alternatively, or in addition, the means of supplying a current through the device may incorporate capacitive and/or pseudo-capacitive electrodes. Electrode 130 and node 160 are electrically coupled by a power supply 120. By applying power using the power supply 120, an electrical field is generated within the fluid-filled conduit 110. Due to the zeta potential between the liquid 140 and the interior surfaces of the conduit 110, a body force is imposed on fluid 140 that is directed from the inlet toward the outlet of the conduit 110. This body force results in a net flow, Q, of the fluid 140 from the reservoir 150 through the conduit 110 and the node 160.

The conduit 110 includes an inlet and an outlet, which allow a liquid to enter and exit the conduit 110. The body of the conduit 110 may comprise any structure capable of directing a flow of a liquid between the inlet and outlet. Inlet and outlet are relative terms, where a fluid inside the conduit 110 flows from the inlet to the outlet. If flow is reversed, the inlet becomes the outlet, and the outlet becomes the inlet. The conduit 110 is not limited to any particular shape or structure (e.g., a right regular cylinder). Moreover, the conduit 110 may have any cross sectional shape or area, and its shape and area may vary along the length of the conduit 110.

Moreover, the conduit 110 may be substantially open inside, or it may be internally subdivided along its length. For example, an interior region in the conduit 110 may include a bundle of capillaries. Alternatively, or additionally, the conduit 110 may contain porous material and have any combination of sections or subdivisions or porous materials along its length. Inclusion of porous material, sections, and subdivisions may be desirable to increase the interior surface area of the conduit 110, effectively increasing the cross-sectional area of the conduit 110 while maintaining a small pore scale. The interior surface of the conduit 110, or at least a portion thereof, displays a zeta potential when wetted with a liquid. Preferably, any structures, subdivisions, or porous materials within the conduit 110 that also comprise the interior surface display a zeta potential when wetted with a liquid.

For a right regular circular conduit (e.g., a capillary), the flow rate is given by:

$$Q = \pi \int_0^R r^2 \frac{-du}{dr} dr,$$

where R is the radius of the conduit and du/dr is the shear rate due to the radial velocity profile that is equal to some function of the shear stress. For a Newtonian liquid, the shear rate is equal to the shear stress divided by the viscosity. But for a non-Newtonian liquid, used here, the shear rate is a non-linear function of the shear stress.

A liquid that exhibits a non-linear relationship between shear rate and shear stress is called a non-Newtonian liquid.

The variety and behavior of non-Newtonian liquids are treated in many textbooks [see, e.g., *Foundations of Colloid Science Vol. II*, R. J. Hunter (Oxford Univ. Press, Oxford, 1989), pp. 994-1002]. Accordingly, many types of non-Newtonian fluids are well known, including liquids that exhibit pseudoplastic (shear thinning) behavior, liquids that exhibit dilatant (shear thickening) behavior, and liquids that exhibit a yield stress or Bingham plastic behavior.

Pseudoplastic liquids tend to exhibit a low viscosity under high-stress conditions and a high viscosity under low-stress conditions, showing a negligible yield value and a viscosity that decreases with increasing shear stress. Meter's functional, as cited in Hunter and referenced to Boger [D. V. Boger, "Demonstration of upper and lower Newtonian fluid behavior in a pseudoplastic fluid," Nature vol. 265, pp. 126-128 (1977)], is commonly used to describe the relation between shear stress and shear rate for a pseudoplastic non-Newtonian liquid. This relationship can be expressed as:

$$\frac{-du}{dr} = \frac{\tau}{\eta_\infty + (\eta_o - \eta_\infty)/(1 + (\tau/\tau_o)^{\alpha-1})}.$$

In this functional, $\tau$ is the shear stress; $\eta_\infty$ and $\eta_0$ are the so-called high-stress and zero-stress limiting values of the dynamic viscosity, respectively; $\alpha$ is a numerical factor termed the power-law-value, which is greater than unity for a pseudoplastic liquid; and $\tau_0$ is the so-called critical shear stress. The denominator on the right-hand-side of Meter's functional gives the viscosity as a function of shear stress. At low shear stress (e.g., $\tau<<\tau_0$), Meter's functional can be approximated as a Newtonian liquid having a shear rate equal to the shear stress divided by the zero-stress viscosity, $\eta_0$. Whereas at high shear stress (e.g., $\tau>>\tau_0$), Meter's functional can be approximated as a Newtonian liquid having shear rate proportional to the shear stress divided by high-stress viscosity, $\eta_\infty$.

In one embodiment, the non-Newtonian liquid used in the electrokinetic device is or comprises a pseudoplastic liquid. The pseudoplastic liquid may be created by combining an additive with a solvent liquid, where the additive may comprise an additive liquid, and additive solid, or a combination of additive liquids and/or solids. In one embodiment, the high-stress viscosity, $\tau_\infty$, of the pseudoplastic liquid is less than twice the viscosity of the solvent liquid, and preferably about equal to the viscosity of the solvent liquid. In another embodiment, the zero-stress viscosity, $\eta_0$, of the pseudoplastic liquid is more than 10 times the high-stress viscosity of the pseudoplastic liquid, and preferably more than 100 times the high-stress viscosity, and most preferably more than 1000 times the high-stress viscosity. In another embodiment, the power-law-value, $\alpha$, of the pseudoplastic liquid is greater than 2, and preferably greater than 3, and most preferably greater than 4.

In one embodiment in which a pseudoplastic liquid is used in the electrokinetic device, the maximum pressure-driven shear stress is less than 4 times the critical shear stress, preferably less than 2 times the critical shear stress, and most preferably less than the critical shear stress. In another embodiment, the maximum electroosmotic flow shear stress is greater than one-half the high-limit shear stress, preferably greater than twice the high-limit shear stress, and most preferably greater than 10 times the high-limit shear stress.

As a specific example of a pseudoplastic liquid, Boger reports data for an aqueous polyacrylic acid solution that exhibits pseudoplastic behavior. Fitting Boger's data to Meter's functional yields values of $\eta_\infty$ of about 0.9 mPa-sec (or 0.9 centipoise, about equal to the viscosity of water), $\eta_0$ of about 3000 mPa-sec, $\alpha$ of about 3.5, and $\tau_0$ of about 0.3 Pascal. For this example, the high-limit shear stress is about 16 Pascal, which is taken to be the value of the shear stress giving a viscosity that is twice the high-stress viscosity.

Although specific examples of non-Newtonian liquids are provided, the electrokinetic devices described herein can be used with any non-Newtonian liquid having appropriate physical properties for a given application. Examples of suitable non-Newtonian fluids for use with embodiments of the present invention include:

Polyacylamide or polyacrylamide-co-acrylate in water (e.g., nominal concentration in the range of 2 to 500 ppm). Suitable concentrated solutions of polyacrylamides or partially hydrolyized polyacrylamides are commercially available under the Dow Chemical trademark SEPARAN.

Polyacrylic acid in water (e.g., nominal concentration in the range of 1 to 2000 ppm).

Carboxymethylcellulose, carboxyethylcellulose, carboxypropylcellulose, or other compounds in the carboxylated-cellulose family in water (e.g., nominal concentration in the range of 2 to 2000 ppm). Suitable concentrated solutions of carboxylated-celluloses are commercially available under the Hercules trademarks AQUALON and NATROSOL.

Xanthum gum in water (e.g., nominal concentration in the range of 20 to 2000 ppm).

Hydoxymethylcellulose, hydroxyethylcellulose, hydroxypropylcellulose, or other compounds hydroxylated-cellulose family in water (e.g., nominal concentration in the range of 20 to 2000 ppm). Suitable concentrated solutions of hydroxylated-celluloses are commercially available under the Hercules trade name AQUALON.

Polyethylene oxide in water (e.g., nominal concentration of 0.1 to 2.5% by weight).

Hydroxypropyl starch phosphate in water (e.g., nominal concentration of 0.1 to 2.5% by weight). Suitable concentrated solutions are commercially available under the National Starch trade name Structure ZEA.

This list is not exhaustive, however, and any of a wide variety of non-Newtonian fluids could be used. Other compounds giving non-Newtonian behavior in aqueous solution include: carrageen, hydroxypropyl guar, gum arabica, gum tragacanth, sodium alginate, carbomer, carboxyvinyl polymers, and laponite. Non-Newtonian behavior is not limited to aqueous solutions, however, and it can be achieved in both aqueous and organic solutions as well as mixtures thereof.

In one embodiment, the non-Newtonian liquid comprises an additive combined with a solvent liquid, where the solvent liquid exhibits a relatively low viscosity and a relatively high dielectric permittivity. For example, the solvent liquid is preferably a liquid that could be used in a traditional electroosmotic device. In some applications, it may be preferable to dialyze the additive material before combining it with the solvent liquid. For example, this could help to remove contaminant sodium sulfate from sodium polystyrene sulfonate. The additive that gives non-Newtonian behavior to the solvent is preferably chosen to preserve or enhance the zeta potential of an electrokinetic device when used with the solvent liquid.

When used with non-Newtonian liquids, the electrokinetic device shown in FIG. 1 can be operated under various conditions. For example, the device may be pressure-driven, in which the fluid 140 flows through the conduit 110 due to an applied fluid pressure differential between the inlet and the outlet. The device may also be driven by electroosmotic means, in which an applied electric field within the conduit 110 causes electroosmotic flow of the fluid 140 due to the zeta potential on the interior surfaces of the conduit 110. Alternatively, the device may be operated under a combination of pressure-driven and electroosmotic flow conditions. When both a pressure difference and an electric potential difference are imposed between the inlet and outlet of the conduit 110, these differences may be imposed in the same direction or in opposed directions. In this way, the pressure-driven and electroosmotic flows can be made to regulate or compliment each other.

In a pressure-driven example, for laminar flow in a capillary driven by an axial pressure gradient $P_z$, the maximum shear stress occurs at the wall of the capillary and is given by $RP_z/2$, where R is the radius of the capillary. For an axial pressure gradient of 10 psi/cm and a 1-micron inside-diameter capillary, the maximum shear stress is about 1.7 Pascal. With Boger's polyacrylic acid solution, this maximum shear stress is substantially less than the high-limit shear stress; thus, the whole flow is subject to a relatively high viscosity (e.g., of the order the zero-stress viscosity).

In an electroosmotic flow example, with an axial electric field of 100 V/cm through a conduit having a 50-mV zeta potential and filled with an aqueous solution having a 10-mM ionic strength, the maximum shear stress is again at the wall and has a value of about 114 Pascal. Again, with Boger's solution, the maximum shear stress in electroosmotic flow is substantially greater than the high-limit shear stress; thus, nearly the whole electroosmotic flow is subject to the high-stress viscosity (e.g., several thousand times less than the zero-stress viscosity).

In an example case of combined pressure-driven and electroosmotic flow, a pressure difference is externally imposed across the electrokinetically active conduit 110. For example, if the pressure at the outlet of the conduit 110 is lower than at the inlet, the pressure difference can induce siphoning, or leakage, of the fluid 140 through the conduit 110. When the electrokinetic device is continuously powered, the pressure-driven leakage is generally negligible. But in some applications it is preferable to power the electrokinetic device on a low duty cycle instead of continuously. When the device is powered according to a duty cycle, the duty cycle may be modulated using one or more sensor signals, either according to the sensor signals or according to some algorithm that depends on the sensor signals. Under duty cycle conditions, the time-integrated pressure-driven leakage can become an issue. A check valve can be added to control this leakage; however, low flow rate check valves tend to leak themselves. Fortunately, for embodiments of the invention this pressure-driven leakage is reduced by a substantial factor due to the non-Newtonian behavior of the liquid 140.

The operation of an embodiment of the electrokinetic device can be understood in the context of use with a pseudo-plastic non-Newtonian fluid. In electroosmotic flow, the high shear stress at the walls makes the electroosmotic flow rate inversely proportional to the high-stress viscosity. With pressure-driven flow, the relatively low maximum shear stress makes the pressure-driven flow rate inversely proportional to values of viscosity approaching or equal to the zero-stress viscosity. The zero-stress viscosity can be 1000 or more times greater than the high-stress viscosity; hence, the pressure driven flow experiences substantially more viscous flow resistance than the electroosmotic flow.

Used with a non-Newtonian liquid, the electrokinetic device may have one or more of several advantages over such devices with Newtonian liquids. For example, for a given pore scale, use of a non-Newtonian fluid rather than a Newtonian fluid provides a substantial increase in stall pressure (e.g., by 10 to 100 times, or more). Moreover, for a given pore scale, use of a non-Newtonian fluid greatly reduces siphoning and, hence, leakage through the electrokinetic device. A device that uses a Newtonian liquid provides some stall pressure, but it would require a liquid of high ionic strength to operate under ideal electroosmotic conditions (i.e., thin double layer). With a non-Newtonian fluid, the same stall pressure can be obtained with a pore scale that is 10 or more times larger than that of the first conduit. This allows a reduction in ionic strength and thus a reduction in current. The ability to use larger pore-scale materials has the immediate advantage that many more commercially available materials are suitable for use as high-performance electrokinetic devices and the device can be operated at lower conductivity hence at a lower current.

In addition, using a Newtonian liquid, an applied potential is required to achieve some stall pressure. (E.g., with traditional EOF devices, it is common practice to use kilovolts to produce pressures in the range of 1000 psi.) But using a non-Newtonian fluid, the same stall pressure can be achieve using an applied potential that is 10 to 100 times smaller, making high pressure pumping possible without the need for high-voltage power supplies. This reduces the detrimental effects of Joule heating and removes problems associated with the use of high voltage, specifically corona discharge and destructive surface breakdown/arcing.

Figure 2:
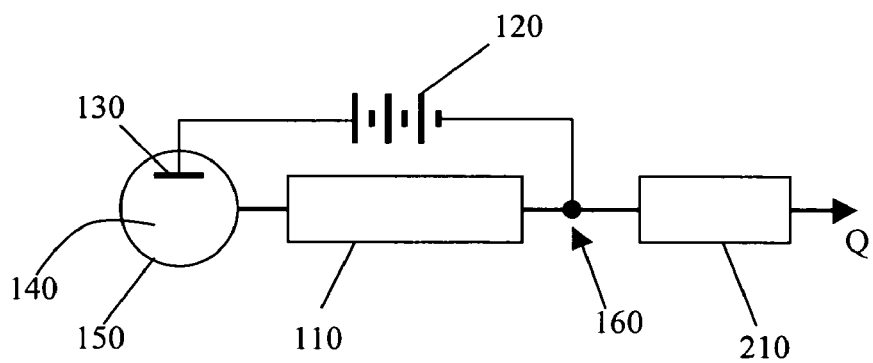
FIG. 2 is a schematic drawing of an electrokinetic pump, in accordance with an embodiment of the invention.

The electrokinetic device illustrated in FIG. 1 can be used in a number of applications. For example, FIG. 2 illustrates how the electrokinetic device of FIG. 1 can be used as a pump to direct flow of a fluid through a fluidic network. In the embodiment shown, a flow resistive element 210 is added in fluidic communication with the conduit 110, downstream of node 160. Although a simple flow resistive element 210 is illustrated, a more complex network of passive and/or active flow elements could be connected to node 160. With the addition of the flow resistive element 210, a liquid pressure is generated between elements 110 and 210. This pressure produces a pressure-driven flow through element 210. In this way, the electrokinetic device is used as an advanced electrokinetic pump. Examples of classical electrokinetic pumps, which recite the use of Newtonian liquids, include U.S. Pat. No. 3,923,426 and U.S. Pat. No. 6,013,164.

Figure 3:
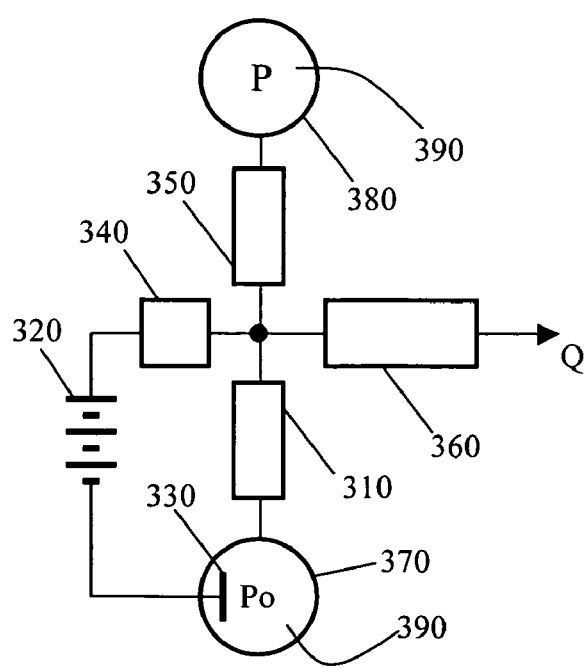
FIG. 3 is a schematic drawing of an electrokinetic flow controller, in accordance with an embodiment of the invention.

Another application of an electrokinetic device in accordance with an embodiment of the invention is in an electroosmotic flow controller. Embodiments of electrokinetic flow controllers are described in co-owned U.S. Patent Publication No. 2002/0189947, which is incorporated by reference in its entirety. FIG. 3 illustrates one embodiment of an electroosmotic flow controller system. In the system, a non-Newtonian liquid 390 is housed in a reservoir 380, which holds the liquid 390 at a pressure P. This pressure P causes pressure-driven flow through flow-resistive element 350 towards the common connection between flow resistive elements 350 and 360, bridge 340, and electrokinetically active conduit 310. Although simple flow resistive elements 350 and 360 are illustrated, a more complex network of passive and/or active flow elements could be used with this system. The conduit 310 is coupled to another reservoir 370, which houses the non-Newtonian liquid 390 at a pressure Po. The reservoir 370 can serve as a source or destination for flow of the liquid 390 through the conduit 310, depending on the direction of flow through the conduit 310. It can be appreciated that the flow through element 350 and conduit 310 towards the common connection is equal to the flow Q out of element 360 away from the common connection, assuming no flow through the bridge 340. Accordingly, by controlling the flow through conduit 310, the flow out of the system, Q, can be controlled.

Electroosmotic flow is used to control the flow of the fluid 390 through the conduit 310. A power supply 320 is coupled between bridge 340 and an electrode 330 that is within reservoir 370 to provide an electric field within the conduit 310. Preferably, the pressure Po in reservoir 370 is less than the pressure P in reservoir 380, and the pressure at the outlet of flow resistive element 360 is also less than pressure P. As such, the pressure-driven flow through element 350 is divided between elements 310 and 360. Application of power to element 310 creates an electroosmotic flow that tends to direct fluid through the conduit 310 towards reservoir 370. The flow through conduit 310 reduces the pressure at the common junction and thus reduces the pressure driven flow through element 360. In this fashion, electrokinetic modulation of element 310 controls the flow through element 360 and thence to any downstream components. Alternatively, the power supply 320 could be configured for electroosmotic flow in the conduit 310 away from reservoir 370 and toward the common junction. Configured this way, the electroosmotic pressure can be used to reduce the pressure-driven flow through the conduit 310 towards the reservoir 370 that normally results from the difference between pressures P and Po.

Advantages of using the non-Newtonian fluid 390 with the flow controller can be appreciated. For example, the nonlinear response to applied pressure changes in electric field greatly extends the range of electroosmotic flow controllers. Use of a non-Newtonian liquid 390 also allows the electrokinetic device to control the pressure-driven flows in the system, thereby controlling the flow Q out of the system.

Figure 4:
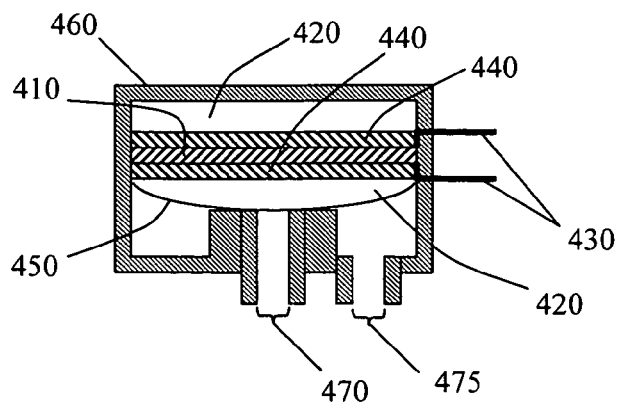
FIG. 4 is a section drawing of an electrokinetically driven diaphragm valve, in accordance with an embodiment of the invention.

In another embodiment, an electrokinetic device in accordance with an embodiment of the invention is used in a diaphragm valve. FIG. 4 illustrates an electrokinetically actuated diaphragm valve. Diaphragm valves are commonly driven mechanically, pneumatically, electromagnetically, and hydraulically. When driven hydraulically, diaphragm valves may be used in a way that actuation of flow in one device affected the flow of some other liquid without mixing of the device liquid with the other liquid. The embodiment shown in FIG. 4 is for explanation purposes, therefore, as diaphragm valves are well known in the arts. Electrokinetic actuation of a diaphragm valve is disclosed for example in U.S. Pat. No. 6,019,882 and U.S. Pat. No. 6,224,728.

To operate the diaphragm valve, a flexible member 450 is moved between an open and a closed position. In a closed position, the flexible member 450 is moved to cover port 470 and thus block liquid communication between port 470 and port 475. In an open position, the flexible member 450 is moved away from the port 470 to allow liquid communication between port 470 and port 475. The flexible member 450 can be a diaphragm, a bellows, or any other known appropriate structure. As illustrated in FIG. 4, the flexible member 450 is actuated by an electrokinetic element 410 filled with a non-Newtonian liquid 420, such as the devices described above. In one embodiment, the electrokinetic element 410 is sandwiched between capacitive electrodes 440, which can be connected to a power supply via lead-outs 430. U.S. Patent Publication No. 2004/0074768, which is incorporated by reference in its entirety, describes the use of capacitive electrodes suitable for this application. This construction avoids the deleterious effects of gaseous and other electrode byproducts.

One problem that fluidically activated diaphragm valves can experience is that once the valve is actuated (i.e., the electrokinetic element is powered and the diaphragm distended), power must be maintained on the pump to maintain the holding pressure that keeps the valve in a closed position. This holding pressure would otherwise be lost due to pressure-driven backflow through the electrokinetic element. In one embodiment, this problem is address by selecting the non-Newtonian liquid 420 to be a pseudoplastic liquid. Following the examples given above, the purely pressure-driven flow rate (i.e., the back leakage through the electrokinetic element 410) can be 100 to 1000 times less than for traditional electrokinetically-actuated diaphragm valves that use a Newtonian liquid. Accordingly, by using a pseudoplastic liquid 420, the diaphragm valve shown in FIG. 4 can be rapidly closed through application of a high voltage potential across leads 430. Because under these high stress conditions a pseudoplastic liquid has a low viscosity, the flow through the electrokinetic element 410 is relatively fast and thus the flexible member 450 is actuated rapidly. Once the valve is closed, there is no significant fluid flow through the element 410; thus, the pseudoplastic liquid is more viscous. Because of this increased viscosity, the applied potential can be reduced by 100 to 1000 times down to a maintenance level that simply compensates for the back-leakage.

In another embodiment, an electrokinetic device using a non-Newtonian liquid is used in a displacement system to dispense or draw-up a second fluid. A flexible or moveable member that is driven mechanically, pneumatically, electromagnetically, or hydraulically may be used to displace a second liquid. Examples of electrokinetically driven displacement systems are shown in FIG. 11 of U.S. Patent Publication No. 2004/0074768 and are described in the corresponding text of the specification. Accordingly, by operably coupling the electrokinetic device to drive the flexible or moveable member hydraulically, a second fluid can be caused to flow. Beneficially, the flexible or moveable member may be used in a way that actuation of the flow of the non-Newtonian fluid in the electrokinetic device affects the flow of the second liquid without mixing of the device liquid with the second liquid.

Figure 5:
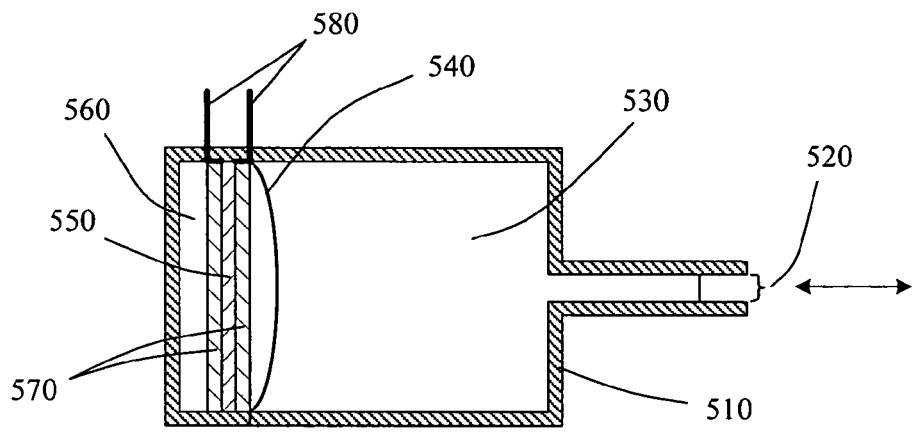
FIG. 5 is a section drawing of an electrokinetically driven displacement system, in accordance with an embodiment of the invention.

FIG. 5 illustrates one embodiment of an electrokinetically driven displacement system. The system comprises a chamber 510 that has at least one opening 520. The chamber 510 is adapted to hold a device liquid 530, which may include any liquid that is intended to be displaced (e.g., dispensed from the chamber 510 or pulled into the chamber 510) by the system. The chamber 510 and the device liquid 530 therein are operably coupled to a flexible member 540 such that movement of the flexible member 540 causes the device liquid 530 to flow through the opening 520 in a direction dictated by the movement of the flexible member 540. The flexible member 540 can be a diaphragm, a bellows, or any other known appropriate structure. Preferably, the flexible member 540 is impermeable to the non-Newtonian liquid 560. This flexible member 540, in turn, is operably coupled to and actuated by an electrokinetic element 550 filled with a non-Newtonian liquid 560, such as the devices described above. In one embodiment, the electrokinetic element 550 is sandwiched between capacitive electrodes 570, which can be connected to a power supply via lead-outs 580. U.S. Patent Publication No. 2004/0074768 describes the use of capacitive electrodes suitable for this application. By controlling the flow of the non-Newtonian liquid 560 through the electrokinetic element 550, an operator can control displacement of the device liquid 530, either into or out of the chamber 510.

Applications of displacement systems such as those described herein include but are not limited to dispensing therapeutic compositions, including drug or other pharmaceutical compounds. For therapeutic applications, dispensing may be done at a relatively low duty cycle. Because siphoning can alter the dosage of the therapeutic composition delivered, siphoning is preferably minimized or completely eliminated through the pumping system. Siphoning in such systems can be caused by minor differences in head-height pressure. With a traditional electrokinetic pumping system using a Newtonian liquid, avoiding siphoning requires some continuous operation of the pump, which consumes electrical power and can also electrochemically evolve the device liquid and thus limit the operational lifetime of the device. Advantageously, by using a non-Newtonian liquid in one embodiment of such a device, back-flow can be substantially reduced due to the high viscosity of a pseudoplastic non-Newtonian liquid under weak pressure-driven flow. In this way, the pumping system requires little or no electrical power to avoid siphoning and thus extends the operational lifetime of the device. This is particularly useful in portable applications that rely on battery power.

To illustrate an embodiment of the invention, measures of stall pressure and unloaded flow rate were performed to compare the performance of a traditional electrokinetic device to that of an embodiment of the invention. In the experiment, the electrokinetically active conduit was a 5 cm long section of 20-micrometer inside diameter silica capillary. One end of the capillary was submerged in a reservoir filled with a working liquid, and the other end of the capillary was fitted into an HPLC 'T'. One of the remaining legs of the 'T' was fitted with a nano-porous glass bridge that terminated in a second reservoir filled with the working liquid. The two reservoirs were equipped with platinum wire electrodes that were connected to a source of direct current. The remaining leg of the 'T' was connected to a second section of silica capillary. The stall pressure was obtained by placing the second capillary vertically as a manometer where the liquid height under stalled flow conditions gave the stall pressure. The open-load flow rate was measured by placing the second capillary in the same plane as the test element and measuring the timed displacement of the liquid effluent.

To test the traditional EOF device, the working liquid was aqueous with 10-mM TRIS and 5-mM acetic acid added, giving a pH of about 8.2. With 100 Volts applied to the test fixture, the steady outlet head-height was observed to be about 42 mm, giving a stall pressure of about 0.06 psi. With 350 Volts applied, an unloaded flow rate of about 8.3 nL/min was measured. These values are consistent with the known zeta potential of silica, the physical dimensions of the test device, and the applied potential.

To test one embodiment of a device according to the invention, the device described above was used instead with a non-Newtonian working liquid. The working liquid was aqueous with 8.33 mM of 42 kilodalton polyacrylic acid and 5 mM TRIS added to give a pH of about 8.2. With 100 Volts applied to the test fixture, the steady head-height was observed to be about 1.898 meters, giving a backpressure of about 2.7 psi. With 350 Volts applied, an unloaded flow rate of about 7.5 nL/min was measured.

Under equal pore-scale (i.e., equal capillary diameter) and equal applied electric potential conditions, using a non-Newtonian liquid in the electrokinetic device realized a nominal 45 times increase in stall pressure compared to a traditional EOF device that uses a Newtonian liquid. The stall pressure in traditional EOF devices is well known to scale inversely with the square of the capillary diameter. Therefore, achieving a stall pressure equal to that found using an embodiment of the invention having a 20-micron inside diameter capillary would require using about a 3-micron inside diameter capillary for the traditional EOF device.

Figure 6:
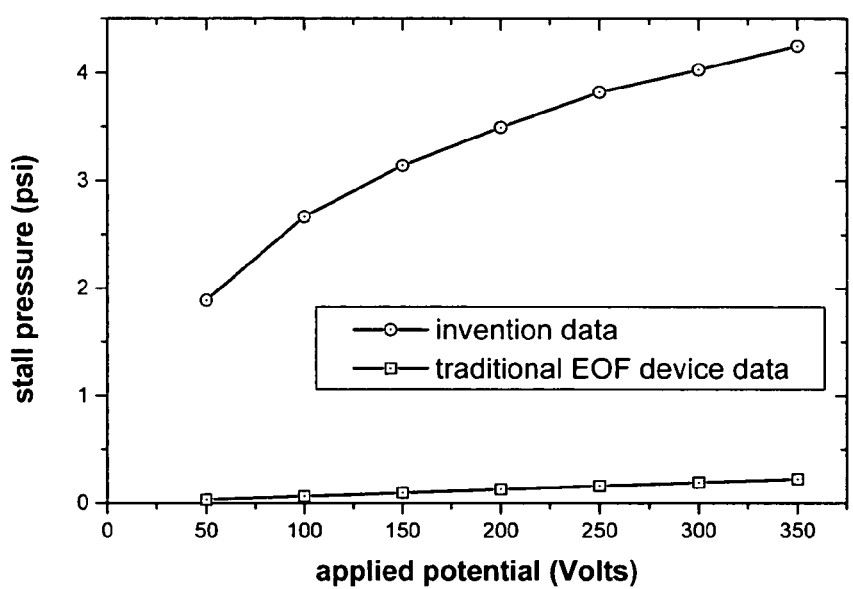
FIG. 6 is a graph of the stall pressure versus applied potential for a traditional electrokinetic device using a Newtonian fluid and for an electrokinetic device using a non-Newtonian fluid.

To further illustrate an embodiment of the invention, the stall pressure was measured as a function of applied potential for both a traditional electrokinetic device and an embodiment of the invention. FIG. 6 is a graph of the stall pressure versus applied potential for a traditional electrokinetic device and for an electrokinetic device using a non-Newtonian liquid. To obtain the data, a conduit having a 5-cm long section of 20-micrometer inside diameter silica capillary was used. One end of the capillary was submerged in a reservoir filled with the working liquid, and the other end of the capillary was fitted into an HPLC 'T'. One of the remaining legs of the 'T' was fitted with a nano-porous glass bridge, which terminated in a second reservoir filled with the working liquid. The two reservoirs were equipped with platinum wire electrodes that were connected to a source of direct current. The last leg of the 'T' was connected to a pressure measurement device.

To test the traditional EOF device, the working liquid was aqueous with 10-mM TRIS and 5-mM acetic acid added, giving a pH of about 8.2. The pressure measurement device was a section of 100-micron inside diameter silica capillary used as a head-height manometer. To test an embodiment of the invention, the working liquid was aqueous with 8.33 mM of 42-kilodalton polyacrylic acid and 5-mM TRIS added to give a pH of about 8.2. The pressure measurement device was a one-meter length of 20-micron inside diameter silica capillary used as a gas-compression manometer. Liquid filled the 'T' and a portion of the second capillary, with air filling the remaining length of the second capillary, and the free end of the second capillary sealed shut. The difference in position of the air-liquid interface between un-powered and powered states of the active element, measured under steady conditions, gives the change in volume of the gas and hence the pressure generated by the test device.

The comparison was performed for applied potential between 50 and 350 Volts and the test results are shown plotted in FIG. 6. According to well-established theory, the pressure produced by a traditional EOF device scales linearly with the applied potential and this is confirmed by the results shown in the graph. The results for the device using the invention show a non-linear variation with increasing applied potential.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

What is claimed is:

1. An electrokinetic device comprising: a conduit having an inlet, an outlet, and an interior surface; a non-Newtonian liquid within the conduit, where at least a portion of the interior surface of the conduit in contact with the non-Newtonian liquid displays a zeta potential; and a plurality of electrodes configured to create an electric potential difference between the inlet and the outlet when connected to a power supply, the electrokinetic device further comprising: a flexible member impermeable to the non-Newtonian liquid and operatively coupled to the conduit, where a flow of liquid through the conduit causes the flexible member to move; and a valve assembly coupled to the flexible member so that flow through the valve assembly is regulated by the position of the flexible member.

2. The device of claim 1, wherein the outlet of the conduit is coupled to the flexible member.

3. The device of claim 2, wherein the flexible member is a diaphragm.

4. The device of claim 2, wherein the flexible member is a bellows.

5. The device of claim 1, wherein the conduit and the valve assembly are isolated so that the non-Newtonian liquid in the conduit cannot mix with a liquid in the valve assembly.

6. The device of claim 1, wherein the conduit is sandwiched between capacitive electrodes configured to supply the electric potential across the conduit.

7. An electrokinetic device comprising: a conduit having an inlet, an outlet, and an interior surface; a non-Newtonian liquid within the conduit, where at least a portion of the interior surface of the conduit in contact with the non-Newtonian liquid displays a zeta potential; and a plurality of electrodes configured to create an electric potential difference between the inlet and the outlet when connected to a power supply, the electrokinetic device further comprising: a flexible member impermeable to the non-Newtonian liquid and operatively coupled to the conduit, where a flow of liquid through the conduit causes the flexible member to move; and a chamber having an opening, wherein when a second liquid is placed within the chamber, the second liquid is operably coupled to the flexible member such that movement of the flexible member causes the second liquid to flow through the opening.

8. The device of claim 7, wherein movement of the flexible member in a first direction causes the chamber to dispense the second liquid to outside the chamber.

9. The device of claim 7, wherein movement of the flexible member in a second direction causes the chamber to draw in an amount of the second liquid from outside the chamber.

10. The device of claim 7, wherein the chamber is filled with the second liquid, and the second liquid comprises a therapeutic composition.

11. The device of claim 7, wherein the conduit and the chamber are isolated so that the non-Newtonian liquid in the conduit cannot mix with a second liquid in the chamber.

12. A kit for causing flow in an electrokinetic device, the kit comprising: a fluidic device including a conduit having an inlet, an outlet, and an interior surface, at least a portion of the interior surface displaying a zeta potential when in contact with a liquid; a plurality of electrodes configured to create an electric potential difference between the inlet and the outlet when connected to a power source; and instructions for using the electrokinetic device, the instructions including an instruction to use a non-Newtonian liquid in the electrokinetic device, the kit further comprising: a flexible member impermeable to the non-Newtonian liquid and operatively coupled to the conduit, where a flow of liquid through the conduit causes the flexible member to move; and a valve assembly coupled to the flexible member so that flow through the valve assembly is regulated by the position of the flexible member.

13. The device of claim 12, wherein the outlet of the conduit is coupled to the flexible member.

14. An electrokinetic device comprising: a liquid having a substantially nonlinear viscosity; an electrokinetic means for displaying a zeta potential between the liquid and a conduit for conducting the liquid; and an electric potential difference configured across the conduit to cause an electroosmotic flow of the liquid within the conduit, wherein the conduit is coupled at one end to a reservoir containing the liquid and at another end to a node in a flow network, the node located in a path of the flow network between a liquid source and a downstream element of the fluid network, whereby flow of liquid through the downstream element is a sum of the flow from the liquid source and the flow from the conduit, and further comprising a flexible member impermeable to the liquid and operatively coupled to the conduit, where a flow of liquid through the conduit causes the flexible member to move; and a valve assembly coupled to the flexible member so that flow through the valve assembly is regulated by the position of the flexible member.

15. A kit for causing flow in an electrokinetic device, the kit comprising: a fluidic device including a conduit having an inlet, an outlet, and an interior surface, at least a portion of the interior surface displaying a zeta potential when in contact with a liquid; a plurality of electrodes configured to create an electric potential difference between the inlet and the outlet when connected to a power supply; and instructions for using the electrokinetic device, the instructions including an instruction to use a non-Newtonian liquid in the electrokinetic device, the kit further comprising: a flexible member impermeable to the non-Newtonian liquid and operatively coupled to the conduit, where a flow of liquid through the conduit causes the flexible member to move; and a chamber having an opening, wherein when a second liquid is placed within the chamber, the second liquid is operably coupled to the flexible member such that movement of the flexible member causes the second liquid to flow through the opening.

* * * * *